United States Patent
Bradford

(10) Patent No.: US 6,251,423 B1
(45) Date of Patent: *Jun. 26, 2001

(54) STERILIZABLE PASTE PRODUCT FOR TOPICAL APPLICATION

(75) Inventor: Colin Raymond Bradford, Keighley (GB)

(73) Assignee: Smith & Nephew PLC, London (GB)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 08/945,483

(22) PCT Filed: May 20, 1996

(86) PCT No.: PCT/GB96/01209

§ 371 Date: Jan. 14, 1998

§ 102(e) Date: Jan. 14, 1998

(87) PCT Pub. No.: WO96/36315

PCT Pub. Date: Nov. 21, 1996

(30) Foreign Application Priority Data

May 20, 1995 (GB) .................................. 9510226

(51) Int. Cl.$^7$ ............................. A61K 9/70; A61K 31/74; A61K 47/30
(52) U.S. Cl. .................... 424/443; 424/78.02; 424/78.08; 424/445; 514/772.2
(58) Field of Search ..................................... 424/443, 445, 424/78.02, 78.08; 514/772.2

(56) References Cited

U.S. PATENT DOCUMENTS 5,266,624 * 11/1993 Prosise et al. ........................ 524/313
5,700,452 * 12/1997 Deckner et al. ........................ 424/59

* cited by examiner

*Primary Examiner*—Shelley A. Dodson
(74) *Attorney, Agent, or Firm*—Larson & Taylor PLC

(57) ABSTRACT

A paste or cream formulation which can be sterilised comprises an emulsion formed of a wax or oil, an emulsifier and water and an insoluble material which forms a gel in the presence of water. A bandage or wound dressing having the paste on a surface thereof is also disclosed. A method of making a sterilisable paste comprises forming an emulsion of oil or wax in water, forming a slurry of a gel-forming material in a polyol and then adding the slurry to the emulsion while mixing.

14 Claims, No Drawings

STERILIZABLE PASTE PRODUCT FOR TOPICAL APPLICATION

The present invention relates to medical products for application to the skin or to a wound, and particularly to products which are applied in the form of a paste.

Paste or cream products for application to the skin for the treatment of medical conditions or wounds are well known; for example zinc oxide is often applied topically in the form of a cream or paste. The cream or paste may be applied by first spreading it onto a bandage or dressing and then applying the bandage or dressing to the skin. This kind of system, i.e. a paste bandage, such as those supplied by Smith and Nephew Healthcare Ltd under their VISCOPASTE trade mark, is often used for the treatment of leg ulcers which are chronic wounds which are often difficult to heal.

Such paste or cream products are usually formulated as emulsions because such formulations have desirable flow and spreading characteristics, feel "creamy" to the touch and are quite resistant to drying out. When the creams are for application to a wound, it is important to avoid the introduction of undesirable organisms, such as bacteria, into the wound and so it is desirable to sterilise the cream or paste before use. However, these emulsions are difficult or impossible to sterilise because they tend to separate when subjected to high temperatures or to sterilising radiation. As an alternative to sterilisation, such formulations may contain preservatives in order to prevent the growth of bacteria in the cream. Unfortunately many patients may be or become sensitive to the preservatives used and such sensitisation may greatly worsen the condition which the cream is intended to treat.

One approach to solving this problem is to formulate the "cream" as a gel, as described in European Patent Application No. 0040378 for example. However gels are known to dry out rapidly and this feature may limit their use in paste bandages which should be flexible when applied to the skin and which should not dry out after application so that the bandage may be removed easily when required. Also, gels, while being soft and pliable, are sometimes difficult to spread easily and evenly. The cream or paste used on a paste bandage must be spreadable both to aid its application to the bandage substrate and to allow the paste to be spread and moulded after its application to the skin or wound.

GB-A-2269745 describes a topical composition for impregnating a bandage which comprises an emulsion comprising one or more fats or oils, one or more emulsifying agents and at least one water-soluble gum and water. No preservative is added.

It is an object of the present invention to provide a sterilisable cream or paste which overcomes some, at least, of the foregoing problems.

According to the invention, a paste formulation comprises an emulsion comprising a wax or oil, at least one emulsifier and water, and a substantially water-insoluble material which forms a gel in the presence of water. The formulation results in a cream or paste which exhibits the desirable properties of an emulsion, in that it is spreadable and has the creamy consistency of an emulsion, yet which does not break down when subjected to normal sterilisation procedures, e.g. steam sterilisation, because the gel stabilises the emulsion. It also exhibits better water retention properties than a conventional gel because water is held both in the emulsion and in the gel.

The term paste used in this document should be taken to include creams and other viscous spreadable compositions such as are often applied to the skin directly or spread onto a bandage or dressing.

The formulation will normally contain as a further component a humectant to reduce the partial vapour pressure of the water in the cream thereby to greatly reduce the rate at which the cream dries out. Suitable humectants are preferably not solvents for the gel-forming material, but are misible with water to a large extent and are preferably suitable for application to the skin. Polyols are especially suitable for the purpose and suitable polyols may include monopropylene glycol but glycerine (glycerol) to British Pharmacopoeia specification is a particularly preferred polyol for this purpose. The polyol may be present in proportions of 25–50% (by weight) of the total formulation; a preferred range is 30–40%.

This relatively high proportion of polyol also ensures that if the paste should dry out to any degree, the resulting paste remains soft and flexible because the glycerine may act as a plasticiser for the polymer. When the paste is applied on a bandage, for example, it may therefore still be removed easily from the skin when the paste has lost water without the need to cut the bandage off. The polyol also has the advantage of functioning to prevent the proliferation of bacteria in the paste when it is in contact with the skin or wound, particularly infected wounds.

The formulation will usually, but not necessarily, contain an active ingredient. Some typical active ingredients which may be used are: zinc oxide, ichthammol, calamine, silver suphadiazine, chlorhexidine acetate, coal tar, chlorhexidine gluconate, metronidazole or other anitbacterial agents, or a combination thereof. Alternative active ingredients may also be found suitable for incorporation into the cream. The concentration of active ingredient in the formulation is typically in the range 0–15% by weight but depends upon the nature of the ingredient. For example, up to about 15 wt %, of zinc oxide may be added; typically 6–10% of zinc oxide is used, possibly in combination with another ingredient such as ichthammol (0–3 wt %) and/or calamine (0–15% wt). lchthammol or calamine may also be used alone. Chlorhexidine acetate is usually used at a concentration of up to 1% by weight; 0.5 wt % is typical.

The emulsion comprises a wax or oil, at least one emulsifier and water. A preferred wax is glyceryl monostearate. It is particularly preferred to use a combination of the glyceryl mono stearate and PEG100 stearate which is available commercially as CITHROL GMS/AS/NA from Croda Universal Ltd. This combination provides both a wax and an emulsifier (PEG 100 stearate) which is especially compatible with the wax, for forming an emulsion in water. It is especially preferred to include a second emulsifier in the formulation to increase the stability of the emulsion. A preferred second emulsifier is a PEG20 stearate, such as CITHROL 1OMS which is supplied by Croda Universal Ltd. The total concentration of emulsifier in the cream should normally be in the range of from 3– 15%. Where two emulsifiers are used, one may be present in a greater concentration than the other. Where the wax/emulsifier combination described above is used, the concentration of CITHROL GMS/AS/NA is usually about five times that of the CITHROL 1OMS.

The water-insoluble material forms a gel with the water of the formulation. The material is therefore hydrophilic but does not dissolve in water to any great extent. The material is most preferably a polymeric material which is a water-absorbing non water-soluble polymer. However non polymeric materials which form gels with water and which are stable at elevated temperatures could also be used, e.g. clays such as kaolin or bentonite. Preferred polymers are superabsorbent polymers such as those disclosed in WO-92/

16245 and comprise hydrophilic cellulose derivatives which have been partially cross-linked to form a three dimensional structure. Suitable cross-linked cellulose derivatives include those of the hydroxy lower alkyl celluloses, wherein the alkyl group contains from 1 to 6 carbon atoms, e.g. hydroxyethyl cellulose or hydroxypropylcellulose, or the carboxycelluloses e.g. carboxymethyl hydroxyethyl cellulose or carboxymethylcellulose. A particularly preferred polymer is a partially cross-linked sodium carboxymethylcellulose supplied as AKUCELL X181by Akzo Chemicals B.V. This polymer is a superabsorbent polymer in that it may absorb at least ten times its own weight of water. The cross-linked structure of the polymer prevents it from dissolving in water but water is easily absorbed into and held within the three-dimensional structure of the polymer to form a gel. Water is lost less rapidly from such a gel than from a solution and this is advantageous in slowing or preventing the drying out of the cream formulation. The polymer content of the formulation is normally less than 10%, preferably in the range from 0.5–5.0% by weight, and, in preferred formulations, usually will be between 1.0% and 2%.

The present invention also provides a method of making a cream or paste, comprising the steps of forming an emulsion of a wax or oil in water in the presence of an emulsifier; forming a slurry of a water-absorbing, substantially water-insoluble polymer with a polyol and then adding said slurry to said emulsion with rapid mixing. In this way the gel-forming polymer is properly dispersed before it forms a gel with the water of the emulsion, thus minimising lumps. The emulsion-forming composition may be heated to a temperature which provides for optimal dispersion of the emulsifier and emulsification of the wax or oil.

Preferably the emulsion also contains up to 40% (by weight of the total formulation) of a polyol, which is preferably glycerol. The active ingredient, e.g. zinc oxide, if used, is preferably added to the emulsion, with rapid mixing, prior to the addition of the slurry but it may be added to the finished paste if necessary. In the latter case, care must be taken to avoid mixing too aggressively which may result in breaking the emulsion. Mixing should, however, be sufficient to disperse the ingredient as homogeneously as possible.

The paste may be sterilised. Sterilisation reduces the viscosity of the paste or cream. The formulation should be selected, by varying the polymer content, to provide the desired flow properties of the finished product. That is, if the product is intended to be sterilised, then the formulation should be chosen to give a product of relatively high viscosity/elasticity before sterilisation. If the product is not intended to be sterilised then the formulation should be adjusted, by selecting an appropriate low polymer content, to give a product having the desired flow properties of the finished product. The emulsion content determines the handling properties and feel of the paste, higher emulsion content leading to increased spreadability and creaminess.

The paste may be packaged into tubes, tubs or other suitable forms of container for storage or it may be spread onto a substrate and then subsequently packaged. Suitable substrates include dressings, including film dressings, and bandages.

A paste according to the invention and its method of manufacture is described in the following Examples.

EXAMPLES 5 paste formulations were made up with the following formulations shown in Table 1.

TABLE 1

| EXAMPLE | 1 | 2 | 3 | 4 | 5 |
|---|---|---|---|---|---|
| Slurry: | | | | | |
| AKUCELL X 181 (cross-linked sodium carboxymethyl cellulose | 1.7 | 2.0 | 2.0 | 1.7 | 2.0 |
| Glycerine B.P. | 10.0 | 10.0 | 10.0 | 10.0 | 10.0 |
| Emulsion: | | | | | |
| Deionised water | 42.3 | 46.0 | 42.9 | 39.3 | 52.0 |
| Glycerine B.P. | 30.0 | 30.0 | 30.0 | 30.0 | 30.0 |
| CITHROL GMS/AS/NA (glyceryl monostearate incorporating PEG 100 stearate) | 5.0 | 2.5 | 10.0 | 5.0 | 5.0 |
| CITHROL 10 MS (PEG 20 stearate) | 1.0 | 0.5 | 2.0 | 1.0 | 1.0 |
| Active Inaredient: | | | | | |
| Zinc Oxide B.P. | 10.0 | 7.0 | 2.0 | 10.0 | — |
| Ichthammol | — | 2.0 | — | — | — |
| Silver Sulphadiazine | — | — | 1.0 | — | — |
| Sodium Chloride | — | — | 0.1 | — | — |
| Refined coal tar | — | — | — | 3.0 | — |

The pastes of Examples 1–5 were made using the following general method:

To form the emulsion, the two CITHROLs were added to the water which was then heated to approximately 65° C. until the CITHROLs had formed a solution. The glycerine was then added to the solution. The mixture was then mixed under shear whilst maintaining the raised temperature and then allowed to cool to room temperature under slow stirring. The active ingredient was added to the cooled emulsion with high shear mixing until it was fully dispersed. In Example 3, the sodium chloride was dissolved in the water used to form the emulsion.

The slurry is formed by rapidly mixing the polymer and glycerine together and it is then added to the emulsion with rapid mixing until the gel is fully formed. When glycerine is used as a dispersant for the polymer, as in all three cases exemplified here, the gel is usually formed over a period of about 30–40 seconds. If monopropylene glycol is used instead of glycerine, the gel forms much more quickly, in less than seconds. The longer time is preferred because the gel forming polymer may then be fully mixed into the emulsion before gel formation is complete.

In Example 4, which contains refined coal tar which is insoluble in water, it has been found that the coal tar may be mixed into the freshly gelled paste within a short period after manufacture, e.g. up to two hours. Mixing of the coal tar into the paste should be just sufficient to disperse the coal tar homogeneously. The viscosity of the paste may continue to increase for several hours after mixing and so if any ingredient is added at that stage it should be added whilst the paste is of sufficiently low viscosity to enable effective mixing. Example contains no active ingredient.

The resulting paste may then be spread onto a bandage or dressing substrate, such as woven cotton gauze or a non-woven gauze, which is then wound and then sealed into pouches or bags made of heat-stable materials before being steam sterilised. After sterilisation, the paste formulation is of lower viscosity than before sterilisation. The formulation and sterilisation conditions are, however, optimised to give a finished (sterilised) product with suitable flow properties for its intended use as a paste bandage.

What is claimed is:

1. A paste formulation for topical application to a body having a creamy consistency and which reduces drying out, said paste formulation comprising:
   (a) an emulsion of a wax or oil in an aqueous gel of a water-insoluble polymeric material together with at least one emulsifier; and
   (b) an active medicinal ingredient which is topically applicable to the body.

2. A paste formulation as claimed in claim 1, wherein said polymeric material comprises a cellulose derivative.

3. A paste formulation as claimed in claim 2, wherein said cellulose derivative comprises a partially cross-linked carboxymethyl cellulose derivative.

4. A paste formulation as claimed in claim 1, wherein said polymeric material is present in the proportion of 0.5%–4.0% by weight of the paste.

5. A paste formulation as claimed in claim 4, wherein said polymeric material is present in the proportion of 1%–2% by weight of the paste.

6. A paste formulation as claimed in claim 1, further comprising a polyol.

7. A paste formulation as claimed in claim 1, comprising more than one emulsifier.

8. A paste formulation as claimed in claim 1 wherein the emulsifier(s) comprise(s) up to 15% by weight of the paste.

9. A paste formulation as claimed in claim 8, wherein the emulsifier(s) is present in the proportion of from 3% to 12% by weight of the paste.

10. A paste formulation as claimed in claim 1, further comprising an additional active ingredient.

11. A paste formulation as claimed on claim 1, wherein said active ingredient comprises at least one of: zinc oxide, ichthammol, calamine, silver sulphadiazine, chlorhexidine acetate, coal tar chlorhexidine gluconate or metronidazole.

12. A bandage or wound dressing for a body comprising:
   a substrate layer, and
   a paste on at least one surface of said substrate layer, said paste being for a topical application to the body and having a creamy consistency and which reduces drying out, said paste comprising:
      (a) an emulsion of a wax or oil in an aqueous gel of a water-insoluble polymeric material together with at least one emulsifier; and
      (b) an active medicinal ingredient which is topically applicable to the body.

13. A method of manufacturing a paste, said paste being used for topical application to a body, having a creamy consistency and reducing driving out, said method comprising the steps of:
   (a) forming a wax- or oil-in-water emulsion of a wax or oil in water in the presence of an emulsifier;
   (b) forming a slurry in a polyol of a water-insoluble polymer which forms a gel in the presence of water;
   (c) adding said slurry to said emulsion with rapid mixing to form the paste; and
   (d) adding an active medicinal ingredient to one of the formed slurry, emulsion or paste.

14. A method as claimed in claim 13, further comprising the step of sterilising said paste.

* * * * *